(12) United States Patent
Bille

(10) Patent No.: US 7,717,906 B2
(45) Date of Patent: May 18, 2010

(54) SYSTEM AND METHOD FOR PHOTOABLATION USING MULTIPLE FOCAL POINTS WITH ROTATING BEAM SPLITTER

(75) Inventor: Josef Bille, Heidelberg (DE)

(73) Assignee: Technolas Perfect Vision GmbH, Heidelberg (DE)

(*) Notice: Subject to any disclaimer, the term of this patent is extended or adjusted under 35 U.S.C. 154(b) by 281 days.

(21) Appl. No.: 11/682,976

(22) Filed: Mar. 7, 2007

(65) Prior Publication Data

US 2007/0179479 A1    Aug. 2, 2007

Related U.S. Application Data

(63) Continuation-in-part of application No. 11/190,052, filed on Jul. 26, 2005, which is a continuation-in-part of application No. 11/033,967, filed on Jan. 12, 2005, now Pat. No. 7,232,436, which is a continuation-in-part of application No. 10/293,226, filed on Nov. 13, 2002, now Pat. No. 6,887,232.

(51) Int. Cl.
*A61B 18/20* (2006.01)

(52) U.S. Cl. ............... 606/4; 606/10; 128/898

(58) Field of Classification Search ............ 606/4–6, 606/10–12; 128/898
See application file for complete search history.

(56) References Cited

U.S. PATENT DOCUMENTS

| | | | |
|---|---|---|---|
| 4,391,275 A | 7/1983 | Fankhauser et al. | |
| 4,718,418 A * | 1/1988 | L'Esperance, Jr. | ............. 606/5 |
| 4,770,172 A | 9/1988 | L'Esperance, Jr. | |
| 4,907,586 A | 3/1990 | Bille et al. | |
| 4,988,348 A | 1/1991 | Bille | |
| 6,210,401 B1 * | 4/2001 | Lai | ............. 606/12 |
| 6,413,251 B1 | 7/2002 | Williams | |
| 6,428,533 B1 | 8/2002 | Bille | |
| 6,897,405 B2 | 5/2005 | Cheng et al. | |
| 6,984,227 B2 | 1/2006 | Munnerlyn et al. | |
| 6,997,923 B2 * | 2/2006 | Anderson et al. | ............. 606/9 |
| 7,101,364 B2 * | 9/2006 | Bille | ............. 606/5 |

FOREIGN PATENT DOCUMENTS

| | | |
|---|---|---|
| EP | 1419752 A1 | 5/2004 |
| WO | 0137769 A1 | 5/2001 |

\* cited by examiner

*Primary Examiner*—Ahmed M Farah
(74) *Attorney, Agent, or Firm*—Nydegger & Associates

(57) ABSTRACT

A system and method for performing ophthalmic surgery requires splitting a laser beam into a pattern having a plurality of focal points. The pattern is then moved along a spiral path according to a predetermined, two-phase protocol. In the first phase, a radial spacing "$\Delta r$" between spiral lines, and the velocity of the pattern "$r\omega$" are held constant as the radius "$r$" is decreased from $r_1$ to $r_2$. In the second phase the angular velocity "$\omega$" is held constant and the radial spacing "$\Delta r$" is proportionally increased as "$r$" is further decreased from $r_2$ to $r_3$. Additional LIOB is required both inside $r_3$, as r is reduced to zero and, then, along the periphery of the treatment area for a rim cut at $r_1$.

19 Claims, 1 Drawing Sheet

SYSTEM AND METHOD FOR PHOTOABLATION USING MULTIPLE FOCAL POINTS WITH ROTATING BEAM SPLITTER

This application is a continuation-in-part of pending application Ser. No. 11/190,052 filed Jul. 26, 2005, which is a continuation-in-part of application Ser. No. 11/033,967 filed Jan. 12, 2005 now U.S. Pat. No. 7,232,436, which is a continuation-in-part of application Ser. No. 10/293,226, filed Nov. 13, 2002, which issued as U.S. Pat. No. 6,887,232 on May 3, 2005. The contents of application Ser. Nos. 11/190,052 and 11/033,967, and issued U.S. Pat. No. 6,887,232, are incorporated herein by reference.

FIELD OF THE INVENTION

The present invention pertains generally to systems and methods for performing ophthalmic surgery. More particularly, the present invention pertains to systems and methods wherein pulses of a femtosecond laser beam are split into a pattern having a plurality of focal points. The present invention is particularly, but not exclusively, useful for systems and methods wherein the movement and orientation of a focal point pattern are coordinated to maximize the efficiency of laser induced optical breakdown (LIOB) caused by the surgical laser beam.

BACKGROUND OF THE INVENTION

Procedures for ophthalmic laser surgery rely on a phenomenon generally known as Laser Induced Optical Breakdown (LIOB). Specifically, LIOB occurs when a laser pulse is focused to concentrate its energy at a focal point in the tissue that is to be altered. This alteration by LIOB will typically involve the vaporization of tissue and, if uncontrolled, can include unacceptable levels of adverse side effects such as the charring and tearing of the tissue. Obviously, the control of LIOB during a laser surgical procedure is a major concern. One solution for controlling LIOB has been to generate a pulsed laser beam wherein each pulse has a very short duration (e.g. several femtoseconds), and a relatively low, but efficacious, energy level (e.g. 1.5 µJ). For example, U.S. Pat. No. 7,103,077, which issued to Schuhmacher et al. for an invention entitled "System and Method for Measuring and Controlling an Energy of an Ultra-Short Pulse of a Laser Beam," and which is assigned to the same assignee as the present invention, discloses a system and method for controlling energy levels in a pulsed laser beam. In addition to control over LIOB, an effective surgical procedure also requires precise control over the location and movement of laser focal points in the treatment area.

Although presently available laser surgical systems are capable of controlling pulse energy while rapidly pulsing a laser beam, and although they are also capable of moving the focal point relatively rapidly through the tissue to be altered by LIOB, present procedures are still somewhat time consuming. Time, however, is an important consideration; primarily because the patient's eye must remain stabilized during the entire procedure. Consequently, it is desirable to accomplish laser ophthalmic surgery in the shortest possible time. The creation of a larger focal point with greater energy may possibly shorten the time required for surgery but, due to the increased risk for adverse side effects, this solution may be inappropriate or impractical. Perhaps a more appropriate solution is to move the focal point at a faster rate through the tissue. This solution, however, may also be impractical due to mechanical limitations of the laser beam delivery system. Another solution is to simultaneously operate with a plurality of focal points.

U.S. Pat. No. 6,610,050, which issued to Bille for an invention entitled "Laser Beam Delivery System with Multiple Focal Points" (hereinafter the '050 Patent), and which is assigned to the same assignee as the present invention, discloses the use of multiple focal points for ophthalmic laser surgery. In addition to the size of each focal point, and their operational energy levels, the '050 Patent also considers the separation of the focal points as an important operational concern. Once multiple focal points have been established, however, there is still a question as to how they are to be moved. For instance, it is known that a grating (i.e. beam splitter) can be used to very easily split a single laser beam into a plurality of focal points. Regardless how the laser beam may be moved, however, if the grating remains stationary, the resultant pattern will always have the same orientation. For several applications, this may be unacceptable. In particular, this will be so when it is desirable to move the pattern of focal points along a curved path, such as in a spiral path.

In light of the above it is an object of the present invention to provide a system for performing ophthalmic laser surgery that coordinates the orientation of a focal point pattern with its movement through a tissue treatment area. Another object of the present invention is to provide a system for performing ophthalmic laser surgery that maintains a substantially constant focal point density as a pattern of focal points is moved through a tissue treatment area. Still another object of the present invention is to provide a system for performing ophthalmic laser surgery that reduces the time required for performing laser surgery by simultaneously performing LIOB at a plurality of focal points. Yet another object of the present invention is to provide a system for performing ophthalmic laser surgery that is particularly efficacious for creating a flap of corneal tissue. Another object of the present invention is to provide a system and a method for performing ophthalmic laser surgery that is easy to implement, is simple to use, and is comparatively cost effective.

SUMMARY OF THE INVENTION

In accordance with the present invention, a system and its method of operation require a capability for splitting a pulsed laser beam into a plurality of focal points. This plurality of focal points then creates a pattern that is moved along a predetermined path through a tissue treatment area to cause laser induced optical breakdown (LIOB) of the tissue. Importantly, the orientation of the pattern is coordinated with movements of the pattern to maximize the efficiency of LIOB.

For purposes of the present invention, a laser source is provided that will generate a pulsed laser beam having a variable energy level that is in a range between around 1 µJ and approximately 10 µJ. In any event, it must be appreciated that when a beam splitter is employed, the initial energy level of the beam will be proportionately divided between the number of resultant focal points. With this in mind, for most applications using a 1 to 3 beam splitter, the laser beam preferably has an energy level of approximately 4.5 µJ, and each pulse has a duration that is less than one picosecond (i.e. it is a femtosecond laser). Further, it is preferable that pulses in the laser beam be fired approximately every 25 µsec.

As mentioned above, an important aspect of the present invention is that the laser beam is to be split into a plurality of focal points. This is accomplished by a grating (i.e. beam splitter) that is positioned on the path of the laser beam. Although different gratings can be used for this purpose (e.g.

1 to 4; or 1 to 7), a 1 to 3 grating is presently preferred. Specifically, the resultant pattern of focal points is preferably a line of three focal points. Thus, when using a 4.5 µJ beam, each focal point will have an energy level of approximately 1.5 µJ. Also, in the pattern, each focal point is preferably separated from an adjacent focal point by approximately twenty microns (20 µm).

In addition to the laser source and the grating (i.e. beam splitter) just mentioned, the system of the present invention also incorporates an optical scanning unit that will move the pattern of the laser beam along a predetermined path in the tissue treatment area. For this purpose, a computer is provided that is connected directly to the scanning unit. Further, for selected operational applications, the computer can also be connected directly to the grating (beam splitter).

In overview, the operation of the present invention is conducted according to a protocol that defines a sequence of three distinct operational phases, and a final rim cut. In both the first and second phases, the pattern of focal points is moved along a spiral path in the treatment area. Specifically, this spiral path extends inwardly from the periphery of the treatment area through a predetermined distance. In the third phase, the pattern of focal points is then further moved inwardly from the predetermined distance to the center of the treatment area. Movement of the pattern in the third phase can be accomplished in any of three ways. For one, the spiral path of the first and second phases can be continued. For another, the pattern of focal points can be moved along a plurality of substantially parallel linear raster paths. For yet another, the grating (beam splitter) is removed and a single focal point is used. Finally, after the three phases have been completed, the laser beam is used to make a rim cut at the periphery of the treatment area.

Insofar as movement of the focal point pattern on the spiral pattern is concerned, it is computer controlled. More specifically, pattern movement is controlled by the scanning unit with input from the computer, and is defined relative to a central axis. Specifically, pattern movement on the spiral path is characterized by a variably controlled angular velocity "ω", and a variably controlled radius "r" for the laser beam. Actually, as will be appreciated by the skilled artisan, the radius "r" is more accurately defined as a radial distance from the center of the spiral to a point on the spiral path. In terms of these variables, the velocity of the laser beam (i.e. the velocity of the focal point pattern) at any location along the spiral path is equal to the product "rω". Preferably, between each pulse of the laser beam (i.e. every 25 µsec), the pattern is moved through a distance on the path equal to approximately 30 µm.

It was mentioned above that the grating preferably splits the laser beam into a pattern of three linearly aligned focal points. In order to maintain this pattern tangential to the spiral path as it is moved along the path at the velocity "rω", it is also necessary to rotate the grating at the angular velocity "ω". Thus, the computer operationally controls both the optical scanning unit and the grating. Thus, the orientation of the pattern (established by movement of the grating) is synchronized with the movement of the pattern (caused by the optical scanning unit).

As mentioned above, the first two phases of the protocol require the pattern of focal points follow a spiral path. In the first phase, a radial spacing "Δr" between spiral lines, and the product "rω", are held substantially constant. This continues as "r" is decreased from a radius $r_1$ of approximately 4.5 millimeters to a radius $r_2$ of approximately 0.85 millimeters. Simultaneously, in order to keep the product "rω" constant as "r" decreases, the angular velocity "ω" is increased during the first phase. At $r_1$, ω is equal to approximately 38 Hz. At $r_2$, however, ω has been increased to approximately 200 Hz. Further, during the first phase, the radial spacing "Δr" between spiral lines is held constant at approximately 6 µm. The first phase ends at $r_2$.

In the second phase of the protocol, "ω" is held substantially constant (e.g. ω=200 Hz) as "r" is further decreased. In this phase, as "r" is decreased from the radius $r_2$ (0.85 mm) to a radius $r_3$ of approximately 0.5 millimeters, the radial spacing "Δr" between spiral lines is proportionally increased. At $r_2$, Δr is approximately 6 µm, and at $r_3$, Δr has been increased to approximately 10 µm. The second phase ends at $r_3$.

As indicated above, the third phase of the protocol can be accomplished in any of three ways. For one, when $r < r_3$, the third phase can be characterized by a constant angular velocity ω (e.g. ω=200 Hz), and a constant radial spacing Δr (e.g. Δr=10 µm), as r changes from r=$r_3$ to r=0. For another, the third phase can be characterized by movement of the pattern along raster lines on a linear path having a plurality of substantially parallel lines. Note, for this alternate embodiment wherein the pattern is moved along raster lines, the 1 to 3 grating needs to be held stationary, with the three focal point lines oriented substantially perpendicular to the raster lines. In a third embodiment, a single focal point is used with an appropriate energy level (e.g. 1.5 µJ), and there is no specific pattern. Finally, and regardless what methodology is used for the third phase, a rim cut is made around the periphery of the treatment area at r=approximately 4.5 mm. For the rim cut, the grating is removed altogether, and the laser beam is used at a single focal point at a desired energy level (e.g. 3 µJ).

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
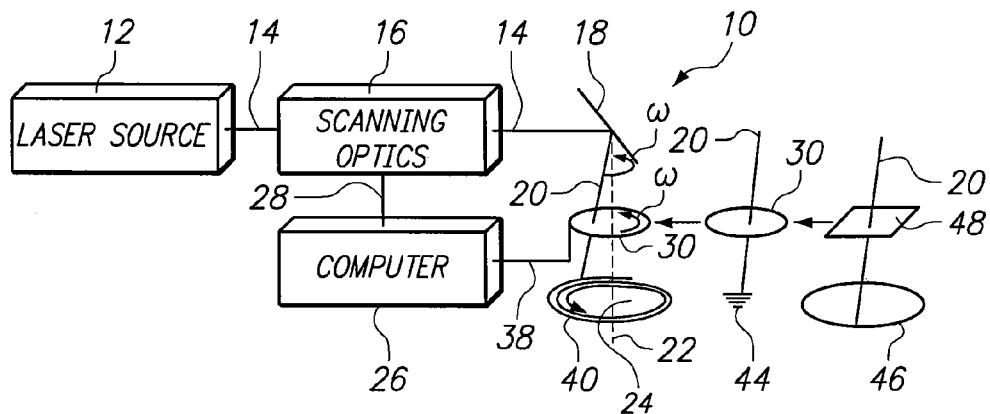
FIG. 1 is a schematic representation of a system for performing laser ophthalmic surgery in accordance with the present invention.

Referring initially to FIG. 1, a system for performing ophthalmic surgery in accordance with the present invention is shown, and is generally designated 10. In FIG. 1 it will be seen that the system 10 includes a laser source 12 for generating a laser beam 14. As envisioned for the present invention, the laser beam 14 will be pulsed, and will have pulses of femtosecond duration (i.e. less than one picosecond duration). Further, each pulse will have an energy level of approximately 4.5 µJ, and the pulses in laser beam 14 will be generated approximately every 25 µsec.

Still referring to FIG. 1, the system 10 is shown to include a scanning optics unit 16 and a turning mirror 18. Together, the unit 16 and the turning mirror 18 are used to direct the laser beam 14 along a beam path 20, relative to a central axis 22, and toward a treatment area 24. For purposes of the present invention, the scanning optics unit 16 includes a system of so-called galvo-mirrors (not shown) that can be operated to move the laser beam path 20. More specifically, it is intended that this movement will be a rotation of the laser beam 14 about the central axis 22 at an angular velocity "ω". Functionally, this control over the laser beam 14 is provided by a computer 26 which is shown electronically connected to the scanning optics unit via a line 28.

Figure 2:
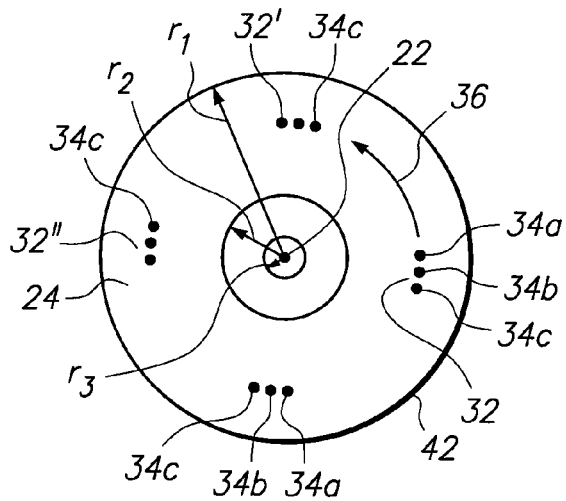
FIG. 2 is a top plan view of a treatment area where the surgery is performed.

As also shown in FIG. 1, the system 10 includes a grating 30 that is used to split the laser beam 14 into a pattern 32 (see FIG. 2). For purposes of the present invention, the pattern 32 will include a plurality of focal points 34. For example, the pattern 32 that is created by grating 30 and shown in FIG. 2 includes three aligned focal points 34a-c. As will be appreciated by the skilled artisan, such a three point pattern 32 results when a "one to three" grating 30 is used. This is only exemplary. Other gratings 30 might be used (e.g. a "one to four" or a "one to seven" grating 30 could be used) with the energy level of the laser beam 14 appropriately adjusted. In the case of a "one to three" grating 30, it will be appreciated that when the energy level of the laser beam 14 is 4.5 µJ, the energy level at each of the respective focal points 34a-c will be 1.5 µJ.

FIG. 2 indicates that the present invention envisions a coordinated relationship between a movement of the pattern 32 and its orientation. To better appreciate this, consider the patterns 32 and 32' shown in FIG. 2. It will then be seen that as the pattern 32 rotates through a 90° arc around the central axis 22 in the direction of arrow 36, to the location indicated for the pattern 32', the orientation of the pattern 32 is also rotated 90°. The same coordination of rotational movement and change in orientation occurs as the pattern 32' is subsequently moved to the location indicated for the pattern 32"; and so on.

Figure 3:
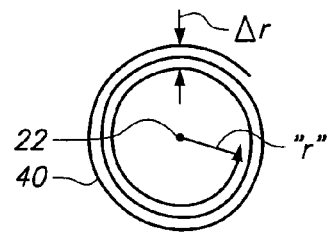
FIG. 3 shows a spiral path followed by laser beam focal points in portions of the treatment area during selected operational phases of the present invention.

The coordination of the rotation and orientation of pattern 32 will be best appreciated with reference back to FIG. 1. There it is shown that the grating 30 is connected via a line 38 to the computer 26. Though not shown, a motor for rotating the grating 30 is positioned in the line 38 between the computer 26 and the grating 30. Thus, the computer 26 is able to control rotations of the grating 30, along with rotations of the beam path 20 of laser beam 14, around the central axis 22. Importantly, in order to effect the coordination of rotation and orientation disclosed above for the pattern 32, the grating 30 and the path 20 of laser beam 14 both need to be rotated in the same direction at the same angular velocity "ω". A consequence of this capability is that, as the radius "r" of the spiral path 40 is diminished during a rotation of the pattern 32 about the central axis 22, the pattern 32 will remain tangential of a spiral path 40 (see FIG. 3).

Operation

A protocol for the operation of the present invention involves a sequence of operational phases. In detail, each phase of the operation is characterized by a unique combination of operational parameters. These include: "r" the radial distance of the pattern 32 from the central axis 22; "ω" the angular velocity of the pattern 32 around the central axis 22; "rω" the tangential velocity of the pattern 32 at a point on the spiral path 40; and "Δr" the radial spacing between lines of the spiral path 40.

In a first phase of the protocol, the pattern 32 of focal points 34a-c is moved inwardly from the periphery 42 of the treatment area 24 along the spiral path 40. During this movement in the first phase, the radial spacing "Δr" between spiral lines, and the product "rω", are held substantially constant in the first phase. This continues as "r" is decreased from a radius $r_1$ of approximately 4.5 millimeters at the periphery 42, to a radius $r_2$ of approximately 0.85 millimeters (see FIG. 2). Simultaneously, as "r" is decreased during the first phase, the angular velocity "ω" is increased. The purpose here is to maintain the product "rω" constant. In doing this, at $r_1$, ω is initially equal to approximately 38 Hz, and at $r_2$, ω has been increased to approximately 200 Hz. Further, during the first phase, the radial spacing "Δr" between spiral lines is held constant at approximately 6 µm.

In the second phase of the protocol, "ω" is no longer varied and, instead, is held substantially constant (e.g. ω=200 Hz) as "r" is further decreased from the radius $r_2$ (0.85 mm) to a radius $r_3$ of approximately 0.5 millimeters (see FIG. 2). During this second phase, however, as the radius "r" decreases, the radial spacing "Δr" between spiral lines of the spiral path 40 is proportionally increased. Specifically, at $r_2$, Δr is approximately 6 µm, and at $r_3$, Δr has been increased to approximately 10 µm.

Figure 4A:
FIG. 4A shows a plurality of linear paths followed by laser beam focal points in a specified portion of the treatment area during an operational phase of the present invention.
Figure 4B:
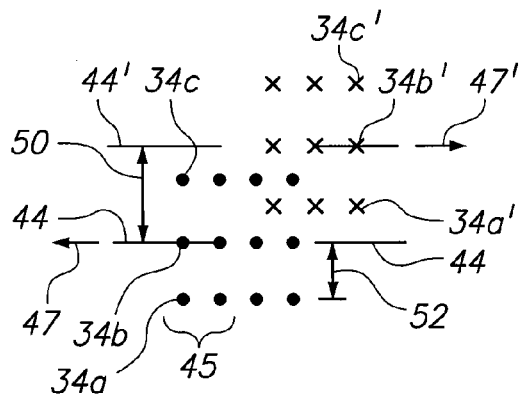
FIG. 4B shows a three point pattern of focal points and the orientation of this pattern to raster lines shown in FIG. 4A.

After the first and second phases of the protocol have been completed, the protocol provides for a third phase. This third phase can be accomplished in any of three ways. For one, when r<$r_3$ (i.e. r<0.5 mm) both "ω" and "Δr" are held constant (e.g. ω=200 Hz and Δr=10 µm) as the spiral pattern is continued. Alternatively, as suggested in FIG. 4A, when r<$r_3$, the pattern 32 can be moved along a linear path 44 having a plurality of substantially parallel raster lines. Note, for this alternate embodiment, the pattern 32 is not rotated and, therefore, the grating 30 needs to be held stationary (see FIG. 1). In this case, it is important that the line of three focal points 34a-c remains perpendicular to the direction of movement of the pattern 32. More specifically, as seen in FIG. 4B, the focal points 34a-c of pattern 32 are substantially perpendicular to the raster line 44 as it moves in the direction of arrow 47. The spacing 52 between focal points 34a, 34b and 34c in the pattern 32 is approximately 20 µm and the advancement 45 of the focal points 34a, 34b and 34c along the raster line 44, between LIOB events, is approximately 10 µm. For the return of pattern 32 along the parallel raster line 44' in the direction of arrow 47', the pattern 32 of focal points 34a', 34b' and 34c', has shifted through a distance 50 that is equal to about 30 µm. In the end, the overall consequence of this is that the distance between LIOB locations is approximately 10 µm. As will be appreciated by the skilled artisan, however, the advancement 45, the distance 50 and the spacing 52 of the focal points 34a-c in the pattern 32 will depend on the energy level being used for the laser beam 14. As noted above, for a third way of performing LIOB when r<$r_3$, the grating 30 is removed. A single focal point laser beam is then moved as desired, at an appropriately reduced energy level. Finally, after the third phase has been completed, a rim cut 46 (see FIG. 1) is made around the periphery 42 of the treatment area 24, at r=approximately 4.5 mm. As indicated for the rim cut 46 in FIG. 1, the grating 30 is removed for the rim cut, and is replaced by a clear glass window 48. The laser beam 14 is then used at a single focal point 34 and at an appropriate energy level (e.g. 3 µJ) to accomplish the rim cut 46.

Figure 5:
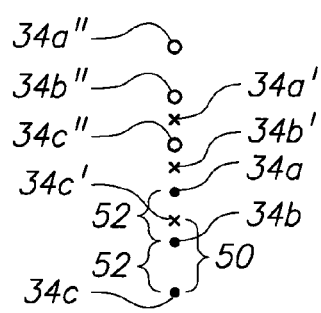
FIG. 5 shows a sequence of laser focal point patterns, as a pattern of focal points is moved along a path during surgery.

Referring now to FIG. 5, a sequence of movements for the pattern 32 during a protocol is shown for a preferred embodiment of the system 10. Recall, it is preferable for a new pulse in the laser beam 14 to be fired approximately every 25 μsec. In this time span between pulses, the pattern 32 is moved through a distance 50 on the path (e.g. spiral path 40 or linear path 44) that is equal to approximately 30 μm. For the rim cut 46, however, the distance 50 is approximately 10 μm. Further, as noted above, the spacing 52 between adjacent focal points 34 in a same pattern 32 will be approximately 20 μm. Consequently, as shown in FIG. 5, for the sequential patterns 32 of focal points 34a-c, 34a'-c', and 34a"-c" there is an overlap in the patterns 32 that results in LIOB at focal points 34 that are located approximately 10 μm from each other. In general, the distance 50 (e.g. 30 μm) will be one and a half times the spacing 52 (e.g. 20 μm).

Figure 6:
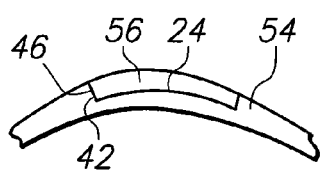
FIG. 6 is a cross-sectional view of a cornea of a patient showing a treatment area in profile.

FIG. 6 shows an intended result of a protocol accomplished on the cornea 54 of a patient in accordance with the present invention. Specifically, the treatment area 24 can be altered by LIOB during the first, second and third phases of the protocol. For the present invention, the treatment area 24 can be either dome shaped, or substantially flat. In either case, the rim cut 46 is then made along selected portions of the periphery 42, around the treatment area 24. The result is a flap 56 of corneal tissue that can be lifted, if desired, for further surgical operations in the treatment area 24.

While the particular System and Method for Photoablation Using Multiple Focal Points with Rotating Beam Splitter as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for performing ophthalmic laser surgery which comprises:
   a source means for generating a pulsed laser beam;
   an optical means for focusing the laser beam into a pattern having a plurality of focal points;
   an optical scanner means for moving the pattern of focal points along a spiral path, wherein movement of the pattern relative to a central axis is characterized by a variable angular velocity "ω", and a variable radius "r"; and
   a computer means, connected to the optical scanner means, for controlling the pattern in a first phase wherein a radial spacing "Δr" between spiral lines, and the product "rω", are held substantially constant as "r" is decreased from a radius $r_1$ to a radius $r_2$, and for controlling the pattern in a second phase wherein "ω" is held constant and the radial spacing "Δr" is proportionally increased as "r" is further decreased from the radius $r_2$ to a radius $r_3$.

2. A system as recited in claim 1 wherein the optical means includes a beam splitter, wherein $r_1$ is approximately 4.5 millimeters, wherein $r_2$ is approximately 0.85 millimeters and wherein $r_3$ is approximately 0.5 millimeters.

3. A system as recited in claim 2 wherein the beam splitter is connected to the computer for synchronized rotation of the beam splitter with the movement of the pattern at the angular velocity ω.

4. A system as recited in claim 2 wherein the beam splitter is a "1 to 3" beam splitter.

5. A system as recited in claim 4 wherein the laser beam has an energy of approximately 4.5 μJ, and the energy at each focal point is approximately 1.5 μJ.

6. A system as recited in claim 5 wherein each focal point in the pattern has a separation from an adjacent focal point of approximately 20 μm.

7. A system as recited in claim 6 wherein each pulse of the pulsed laser beam has a duration less than one picosecond, and wherein a pulse is fired approximately every 25 μsec, and further wherein the pattern is moved through a distance of approximately 30 μm between each pulse.

8. A system as recited in claim 2 wherein the first phase is characterized by changing ω from $\omega_1$=38 Hz to $\omega_2$=200 Hz, as r is correspondingly changed from $r_1$=approximately 4.5 mm to $r_2$=approximately 0.85 mm ($r_1\omega_1$=$r_2\omega_2$=constant).

9. A system as recited in claim 8 wherein the second phase is characterized by a constant ω ($\omega_2$=200 Hz), and a proportional change in the radial spacing Δr, from Δr=6 μm at $r_2$, to Δr=10 μm at r=$r_3$.

10. A system as recited in claim 9 wherein the computer moves the pattern in a third phase characterized by a constant ω (ω=200 Hz) and a constant Δr (Δr=10 μm) as r changes from r=$r_3$ to r=0.

11. A system as recited in claim 9 wherein the computer moves the pattern in a third phase along a linear path characterized by a plurality of substantially parallel lines when r<$r_3$.

12. A system as recited in claim 11 further comprising a clear window, wherein the beam splitter is replaced by the clear window during creation of a rim cut at $r_1$=approximately 4.5 mm.

13. A system as recited in claim 9 wherein the rotating beam splitter is removed during the third phase and the laser beam is moved with a single focal point.

14. A system for performing ophthalmic laser surgery which comprises:
   a source for generating a pulsed laser beam;
   a means for splitting the laser beam into a pattern having a plurality of focal points;
   an optical means for moving the pattern along a path in accordance with a predetermined protocol wherein the path is a spiral path and movement of the pattern relative to a central axis is characterized by a variable angular velocity "ω", and a variable radius "r"; and where in the protocol includes: a first phase wherein a radial spacing "Δr" between spiral lines, and the product "rω", are held substantially constant as "r" is decreased from a radius $r_1$ of approximately 4.5 millimeters to a radius $r_2$ of approximately 0.85 millimeters, and a second phase wherein "ω" is held constant and the radial spacing "Δr" is proportionally increased as "r" is further decreased from the radius $r_2$ of approximately 0.85 millimeters to a radius $r_3$ of approximately 0.5 millimeters; and
   a computer means for synchronizing a movement of the beam splitting means with the movement of the pattern along a predetermined portion of the path.

15. A system as recited in claim 14 wherein the protocol further includes a third phase characterized by a constant angular velocity ω, and a constant radial spacing Δr, as r changes from r =$r_3$ to r =0, and a rim cut where r =approximately 4.5 mm.

16. A system as recited in claim 14 wherein the protocol further includes a third phase characterized by movement of the pattern along a linear path having a plurality of substantially parallel lines when r<$r_3$, and a rim cut where r=approximately 4.5 mm.

17. A method for performing ophthalmic laser surgery which comprises the steps of:
   generating a pulsed laser beam, wherein the laser beam has an energy of approximately 4.5 μJ and each pulse has a duration less than one picosecond, and wherein a pulse is fired approximately every 25 μsec;

splitting each pulse of the laser beam into a pattern having a plurality of focal points, with the energy at each focal point being approximately 1.5 μJ and with each focal point in the pattern having a separation from an adjacent focal point of approximately 20 μm;

moving the pattern of focal points along a spiral path, wherein movement of the pattern relative to a central axis is characterized by a variable angular velocity "ω", and a variable radius "r", and wherein the pattern is moved through a distance of approximately 30 μm between each pulse; and synchronizing the splitting step and the moving step to follow a protocol having a first phase wherein a radial spacing "Δr" between spiral lines, and the product "rω", are held substantially constant as "r" is decreased from a radius $r_1$ of approximately 4.5 millimeters to a radius $r_2$ of approximately 0.85 millimeters, and having a second phase wherein "ω" is held constant and the radial spacing "Δr" is proportionally increased as "r" is further decreased from the radius $r_2$ of approximately 0.85 millimeters to a radius $r_3$ of approximately 0.5 millimeters.

18. A method as recited in claim 17 further comprising the step of including a third phase into the protocol wherein the third phase is characterized by a constant angular velocity ω, and a constant radial spacing Δr, as r changes from r=$r_3$ to r=0, and a rim cut where r=approximately 4.5 mm.

19. A method as recited in claim 17 further comprising the step of including a third phase into the protocol wherein the third phase is characterized by movement of the pattern along a linear path having a plurality of substantially parallel lines when r<$r_3$, and a rim cut where r=approximately 4.5 mm.

* * * * *